United States Patent [19]
Douglas et al.

[11] Patent Number: 6,071,250
[45] Date of Patent: *Jun. 6, 2000

[54] METHODS AND APPARATUS FOR EXPRESSING BODY FLUID FROM AN INCISION

[75] Inventors: Joel S. Douglas, Santa Clara; Jeffrey N. Roe, San Ramon; Henry M. Grage, Danville, all of Calif.

[73] Assignee: Amira Medical, Scotts Valley, Calif.

[*] Notice: This patent is subject to a terminal disclaimer.

[21] Appl. No.: 09/238,140

[22] Filed: Jan. 28, 1999

Related U.S. Application Data

[63] Continuation of application No. 08/858,043, May 16, 1997.

[51] Int. Cl.[7] .......................................................... A61B 5/00
[52] U.S. Cl. .......................................... 600/583; 606/181
[58] Field of Search .................................... 600/573, 576, 600/583; 606/181, 182

[56] References Cited

U.S. PATENT DOCUMENTS

| | | | |
|---|---|---|---|
| D. 254,444 | 3/1980 | Levine | D24/54 |
| 3,030,959 | 4/1962 | Grünert | 128/329 |
| 3,626,929 | 12/1971 | Sanz et al. | 600/583 |
| 3,734,085 | 5/1973 | Russell | 128/36 |
| 3,741,197 | 6/1973 | Sanz et al. | 600/583 |

(List continued on next page.)

FOREIGN PATENT DOCUMENTS

| | | |
|---|---|---|
| 0 212 906 | 4/1987 | European Pat. Off. . |
| 0453283 | 4/1991 | European Pat. Off. . |
| 0 622 046 | 2/1994 | European Pat. Off. . |
| 3708031 | 10/1987 | Germany . |
| WO 8504089 | 9/1985 | WIPO . |
| WO 9510223 | 10/1994 | WIPO . |
| WO 9743962 | 6/1997 | WIPO . |
| 97/42885 | 11/1997 | WIPO . |
| 97/43962 | 11/1997 | WIPO . |

OTHER PUBLICATIONS

Supplemental European Search Report EP 97 92 7654.
Patent Abstract of Japan; Publication No. 0800598; Jan. 9, 1996.
Ash, et al., "A Subcutaneous Capillary Filtrate . . . ," ASAIO Journal, 1993, pp. M699–M705.
Ash, et al., "Subcutaneous Capillary Filtrate . . . ," ASAIO Journal, 1992, pp. M416–M420.
Critical Reviews in Biochemical Engineering, vol. 18, issue 1, 1990, pp. 29–54.
Brace, et al., "Reevaluation of the needle . . . ," Amer Jrnal of Phy, v 229, 1975, pp. 603–607.
Ginsberg., "An Overview of Minimally . . . ," Clinical Chem, v 38, 1992, pp. 1596–1600.
Janle–Swain, et al., "Use of Capillary . . . ," Trans Am Soc Artif Intern Organs, 1987, p. 336–40.
Kayashima, et al., "Suction effusion fluid from . . . ," Amer Phys Soc, 1992, pp. H1623–1626.
Korthuis, et al., "Interstitium & Lymphatic Techniques," pp. 326–327.
Turner, et al., "Diabetes Mellitus: Biosensors for . . . ," Biosensors, 1985, pp. 85–115.

*Primary Examiner*—Cary E. O'Connor
*Assistant Examiner*—Charles Marmor, II
*Attorney, Agent, or Firm*—Burns, Doane, Swecker & Mathis, L.L.P.

[57] ABSTRACT

A sample of a body fluid such as blood or interstitial fluid is obtained from a body by lancing a portion of a user's skin, preferably in an area other than a finger tip, to form an incision. After the needle has been removed from the incision, a force is applied to depress the skin in a manner forming a ring of depressed body tissue in surrounding relationship to the incision, causing the incision to bulge and the sides of the incision to open, whereby body fluid is forced out through the opening of the incision. A stimulator member is mounted to an end of a lancet-carrying housing for applying the force. The stimulator member can be movable relative to the housing, and can be either heated or vibrated to promote movement of the body fluid.

14 Claims, 6 Drawing Sheets

U.S. PATENT DOCUMENTS

| | | | |
|---|---|---|---|
| 4,360,016 | 11/1982 | Sarrine | 600/576 |
| 4,503,856 | 3/1985 | Cornell et al. | 128/314 |
| 4,517,978 | 5/1985 | Levin et al. | 128/314 |
| 4,622,974 | 11/1986 | Coleman et al. | 128/634 |
| 4,627,445 | 12/1986 | Garcia et al. | 600/583 |
| 4,637,403 | 1/1987 | Garcia et al. | 600/583 |
| 4,648,408 | 3/1987 | Hutcheson et al. | 600/583 |
| 4,653,511 | 3/1987 | Goch | 600/576 |
| 4,653,513 | 3/1987 | Dombrowski | 600/578 |
| 4,658,821 | 4/1987 | Chiodo et al. | 128/314 |
| 4,685,463 | 8/1987 | Williams | 128/632 |
| 4,787,398 | 11/1988 | Garcia et al. | 600/583 |
| 4,790,979 | 12/1988 | Terminiello et al. | 422/56 |
| 4,805,623 | 2/1989 | Jobsis | 128/633 |
| 4,850,973 | 7/1989 | Jordan et al. | 604/157 |
| 4,858,607 | 8/1989 | Jordan et al. | 128/314 |
| 4,873,993 | 10/1989 | Meserol et al. | 600/573 |
| 4,883,068 | 11/1989 | Dechow | 600/573 |
| 4,920,977 | 5/1990 | Haynes | 600/583 |
| 4,924,879 | 5/1990 | O'Brien | 128/314 |
| 4,953,552 | 9/1990 | DeMarzo | 128/635 |
| 4,976,724 | 12/1990 | Nieto et al. | 606/182 |
| 4,994,068 | 2/1991 | Hufnagle | 606/181 |
| 5,002,054 | 3/1991 | Ash et al. | 128/635 |
| 5,014,718 | 5/1991 | Mitchen | 600/584 |
| 5,029,583 | 7/1991 | Meserol et al. | 128/633 |
| 5,054,499 | 10/1991 | Swierczek | 600/583 |
| 5,066,859 | 11/1991 | Karkar et al. | 250/339 |
| 5,070,886 | 12/1991 | Mitchen et al. | 600/584 |
| 5,163,442 | 11/1992 | Ono | 600/573 |
| 5,165,418 | 11/1992 | Tankovich | 600/573 |
| 5,201,324 | 4/1993 | Swierczek | 600/583 |
| 5,217,480 | 6/1993 | Haber et al. | 606/182 |
| 5,231,993 | 8/1993 | Haber et al. | 600/583 |
| 5,277,198 | 1/1994 | Kanner et al. | 600/578 |
| 5,318,583 | 6/1994 | Rabenau et al. | 606/182 |
| 5,318,584 | 6/1994 | Lange et al. | 606/182 |
| 5,320,607 | 6/1994 | Ishibashi | 604/115 |
| 5,368,047 | 11/1994 | Suzuki et al. | 600/578 |
| 5,395,387 | 3/1995 | Burns | 606/181 |
| 5,402,798 | 4/1995 | Swierczek et al. | 600/583 |
| 5,421,816 | 6/1995 | Lipkovker | 604/20 |
| 5,445,611 | 8/1995 | Eppstein et al. | 604/49 |
| 5,458,140 | 10/1995 | Eppstein et al. | 600/584 |
| 5,569,212 | 10/1996 | Brown | 604/207 |
| 5,582,184 | 12/1996 | Erickson et al. | 600/576 |
| 5,628,309 | 5/1997 | Brown | 128/632 |
| 5,628,764 | 5/1997 | Schraga | 606/182 |
| 5,666,966 | 9/1997 | Horie et al. | 128/760 |
| 5,709,699 | 1/1998 | Warner | 606/181 |
| 5,730,753 | 3/1998 | Morita | 606/181 |
| 5,885,219 | 3/1999 | Nightengale | 600/461 |
| 5,891,053 | 4/1999 | Sesekura | 600/575 |
| 5,916,222 | 6/1999 | Iwasaki et al. | 606/133 |

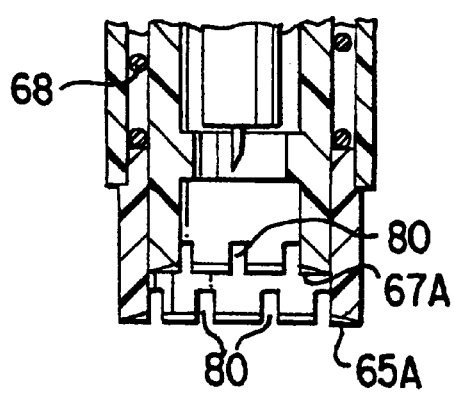 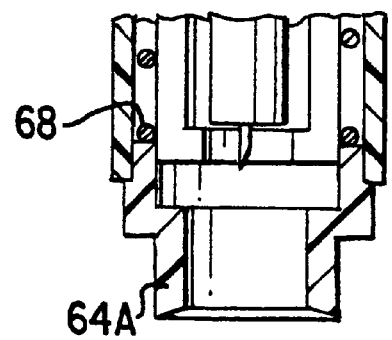
FIG. 7   FIG. 8
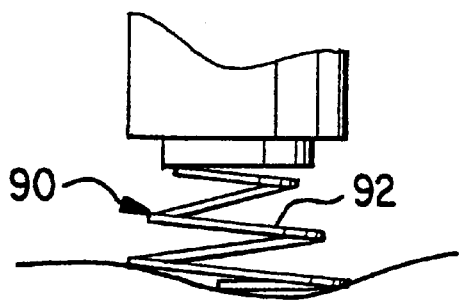 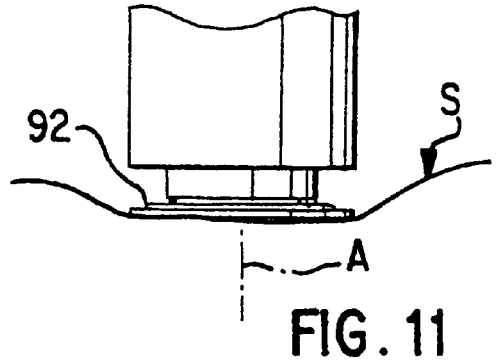
FIG. 9   FIG. 11
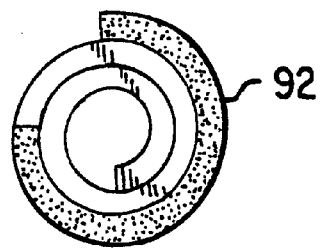 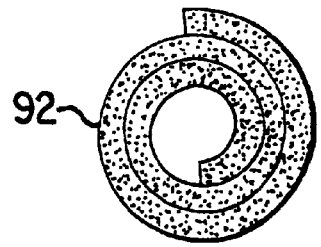
FIG. 10   FIG. 12

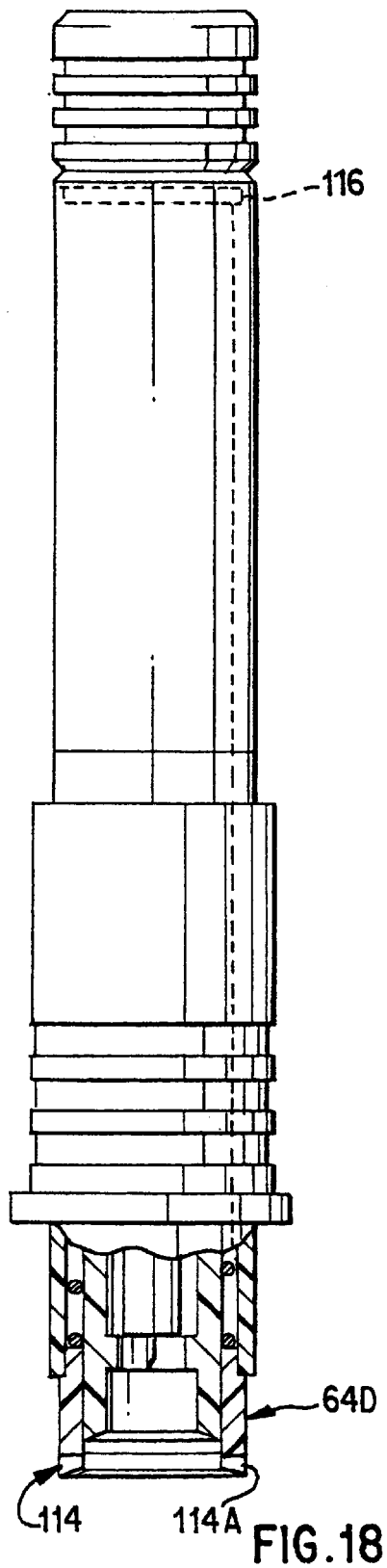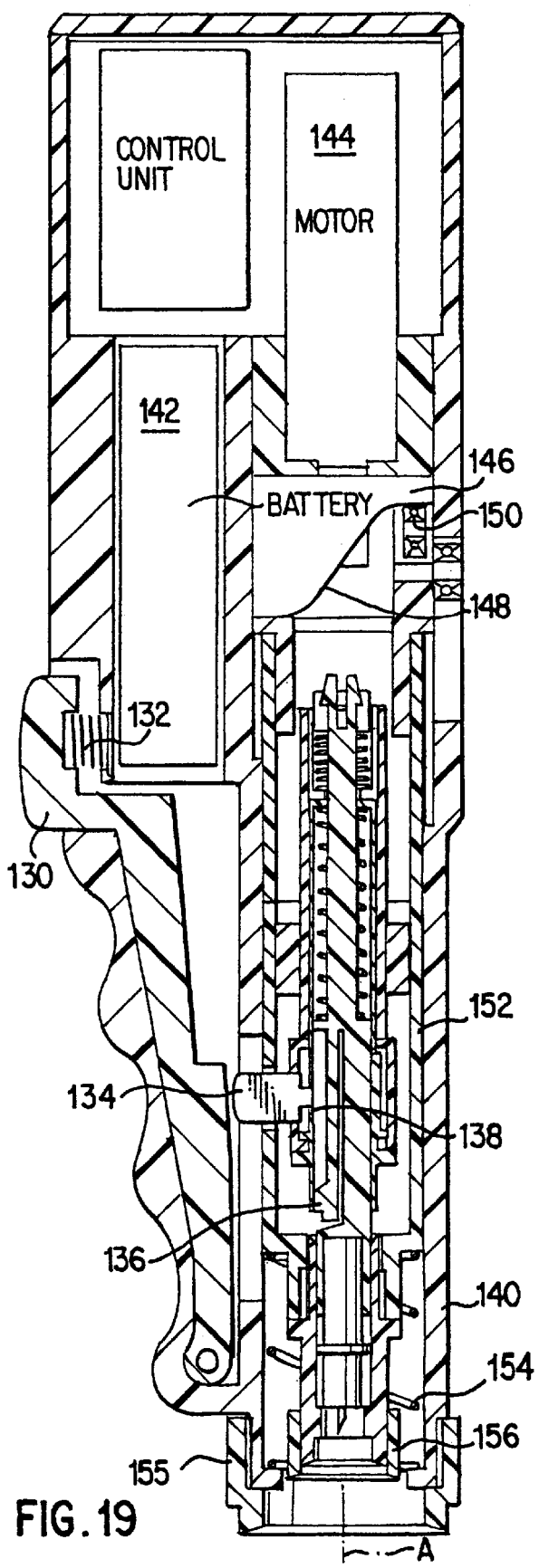

METHODS AND APPARATUS FOR EXPRESSING BODY FLUID FROM AN INCISION

This application is a continuation of application Ser. No. 08/858,043, filed May 16, 1997.

PRIOR APPLICATIONS

This application claims benefit of copending applications Ser. No. 60/017,133 filed May 17, 1996; 60/019,918 filed Jun. 14, 1996; 06/023,658 filed Aug. 1, 1996; 60/028,340 filed Sep. 3, 1996; 08/714,548 filed Sep. 16, 1996; 08/710,456 filed Sep. 17, 1996; and 08/727,074 filed Oct. 8, 1996 the disclosures of which are incorporated herein by reference.

The present invention is related to inventions disclosed in the following commonly assigned U.S. Applications and any subsequently filed continuing or divisional application related thereto: Ser. No. 08/857,680, entitled "Body Fluid sampling Device and Methods of Use"; Ser. No. 08/858,045, entitled "Methods and Apparatus for Sampling Body Fluid"; Ser. No. 08/857,335, entitled "Disposable Element for Use in a Body Fluid Sampling Device"; Ser. No. 08/858,042, entitled "Methods and Apparatus for Sampling and Analyzing Body Fluid"; Ser. No. 08/960,866 entitled "Synchronized Analyte Testing System"; Ser. No. 08/874,468 entitled "Device for Determination of an Analyte in a Body Fluid"; and Ser. No. 29/072,445 entitled "Design for a Test Strip Device". The disclosures of those applications are incorporated herein by reference.

FIELD OF THE INVENTION

The present invention relates to lancing devices and methods for obtaining samples of blood and other fluids from the body for analysis or processing.

BACKGROUND OF THE INVENTION

Many medical procedures in use today require a relatively small sample of blood, in the range of 5–50 μL. It is more cost effective and less traumatic to the patient to obtain such a sample by lancing or piercing the skin at a selected location, such as the finger, to enable the collection of 1 or 2 drops of blood, than by using a phlebotomist to draw a tube of venous blood. With the advent of home use tests such as self monitoring of blood glucose, there is a requirement for a simple procedure which can be performed in any setting by a person needing to test.

Lancets in conventional use generally have a rigid body and a sterile needle which protrudes from one end. The lancet may be used to pierce the skin, thereby enabling the collection of a blood sample from the opening created. The blood is transferred to a test device or collection device. Blood is most commonly taken from the fingertips, where the supply is generally excellent. However, the nerve density in this region causes significant pain in many patients. Sampling of alternate site, such as earlobes and limbs, is sometimes practiced to access sites which are less sensitive. These sites are also less likely to provide excellent blood samples and make blood transfer directly to test devices difficult.

Repeated lancing in limited surface areas (such as fingertips) results in callous formation. This leads to increased difficulty in drawing blood and increased pain.

To reduce the anxiety of piercing the skin and the associated pain, many spring loaded devices have been developed. The following two patents are representative of the devices which were developed in the 1980's for use with home diagnostic test products.

Cornell et al. U.S. Pat. No. 4,503,856 describes a spring loaded lancet injector. The reusable device interfaces with a disposable lancet. The lancet holder may be latched in a retracted position. When the user contacts a release, a spring causes the lancet to pierce the skin at high speed and then retract. The speed is important to reduce the pain associated with the puncture.

Levin et al. U.S. Pat. No. 4,517,978 describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In institutional settings, it is often desirable to collect the sample from the patient and then introduce the sample to a test device in a controlled fashion. Some blood glucose monitoring systems, for example, require that the blood sample be applied to a test device which is in contact with a test instrument. In such situations, bringing the finger of a patient directly to the test device poses some risk of contamination from blood of a previous patient. With such systems, particularly in hospital settings, it is common to lance a patient, collect a sample in a micropipette via capillary action and then deliver the sample from the pipette to the test device.

Haynes U.S. Pat. No. 4,920,977 describes a blood collection assembly with lancet and microcollection tube. This device incorporates a lancet and collection container in a single device. The lancing and collection are two separate activities, but the device is a convenient single disposable unit for situations when sample collection prior to use is desirable. Similar devices are disclosed in Sarrine U.S. Pat. No. 4,360,016, and O'Brien U.S. Pat. No. 4,924,879.

Jordan et al. U.S. Pat. Nos. 4,850,973 and 4,858,607, disclose a combination device which may be alternatively used as a syringe-type injection device and a lancing device with disposable solid needle lancet, depending on configuration.

Lange et al. U.S. Pat. No. 5,318,584 describes a blood lancet device for withdrawing blood for diagnostic purposes. This invention uses a rotary/sliding transmission system to reduce the pain of lancing. The puncture depth is easily and precisely adjustable by the user.

Suzuki et al. U.S. Pat. No. 5,368,047, Dombrowski U.S. Pat. No. 4,654,513 and Ishibashi et al. U.S. Pat. No. 5,320,607 each describe suction-type blood samplers. These devices develop suction between the lancing site and the end of the device when the lancet holding mechanism withdraws after piercing the skin. A flexible gasket around the end of the device helps seal the end around the puncture site until adequate sample is drawn from the puncture site or the user pulls back on the device.

Garcia et al. U.S. Pat. No. 4,637,403 and Haber et al. U.S. Pat. No. 5,217,480, disclose combination lancing and blood collection devices which use a diaphragm to create a vacuum over the wound site.

Erickson et al. U.S. Pat. No. 5,582,184, describes a means of collecting and measuring body fluids. This system uses a coaxial hollow lancet and capillary tube disposed within a spacer member. The spacer member limits the depth of lancet penetration, and compresses body tissue around the lancet while the lancet is in the skin, for improving the flow of interstitial fluid to the incision. However, the incision may tend to close around the lancet, thereby limiting the amount of body fluid that can be obtained.

Single use devices have also been developed for single use tests, i.e. home cholesterol testing, and for institutional use to eliminate cross-patient contamination multi-patient use. Crossman et al. U.S. Pat. No. 4,869,249, and Swierczek U.S. Pat. No. 5,402,798, also disclose disposable, single use lancing devices.

U.S. Pat. Nos. 5,421,816; 5,445,611 and 5,458,140 disclose, as a replacement for invasive sampling, the use of ultrasound to act as a pump for expressing interstitial fluid directly through intact (i.e., non-lanced) skin. The amount of fluid which can be obtained by way of such non-invasive vibration is minimal, however.

The disclosures of the above patents are incorporated herein by reference.

Even with the many improvements which have been made, the pain associated with lancing remains a significant issue for many patients. The need for blood sampling and the fear of the associated pain is also a major obstacle for the millions of diagnosed diabetics, who do not adequately monitor their blood glucose due to the pain involved. Moreover, lancing to obtain a blood sample for other diagnostic applications is becoming more commonplace, and a less painful, minimally invasive device is needed to enhance those applications and make those technologies more acceptable.

An object of the present invention therefore, is to provide a device and a method for obtaining a sample of bodily fluid through the skin which is virtually pain free and minimally invasive, particularly by penetrating less sensitive areas of the skin.

Furthermore, known lancing devices include manually actuable buttons for triggering the lance-driving mechanism once the user has placed the device against his/her skin. Because the user knows the precise instant when the lancet will be triggered and pain will be felt, there is a tendency for the user to jerk or raise the device at the instant of triggering, which can lead to inconsistent skin penetration, or possibly no penetration. Therefore, a further object of the invention is to provide a lancing device which eliminates such a tendency on the part of the user.

Therefore, it is another object of the invention to provide a lancet carrier which eliminates the above-mentioned shortcomings.

Another object of this invention is to provide a method which can result in a sample of either blood or interstitial fluid, depending on the sample site and the penetration depth utilized. While there are no commercially available devices utilizing interstitial fluid (ISF) at this time, there are active efforts to establish the correlation of analytes, such as glucose, in ISF compared to whole blood. If ISF could be readily obtained and correlation is established, ISF may be preferable as a sample since there is no interference of red blood cells or hematocrit adjustment required.

Another object of this invention is to provide a method which can draw a small but adjustable sample, i.e. 3 µL for one test device and 8 µL for another test device, as appropriate.

Another object of this invention is to provide a method by which the drawn sample is collected and may be easily presented to a testing device, regardless of the location of the sample site on the body. This approach helps with infection control in that multiple patients are not brought in contact with a single test instrument; only the sampling device with a disposable patient-contact portion is brought to the test instrument. Alternatively, the disposable portion of a test device may be physically coupled with the sampler so the sample can be brought directly into the test device during sampling. The test device may then be read in a test instrument if appropriate or the testing system can be integrated into the sampler and the test device can provide direct results displayed for the patient.

It is a further object of the invention is to provide a device for minimally invasive sampling comprising a reusable sampler and disposable sample lancet and collection device.

SUMMARY OF THE INVENTION

The present invention involves a method of obtaining a sample of fluid from a body. The method comprises applying a skin-lancing medium against a skin surface to form an incision therein, removing the skin-lancing medium from the incision; and thereafter applying a force to depress the skin in a manner-forming a ring of depressed body tissue in surrounding relationship to the incision, causing the incision to bulge and the sides of the incision to open, whereby body fluid is forced out through the opening of the incision.

The invention also relates to a device for sampling body fluid which comprises a housing having an open end, and a skin lancing mechanism for applying a skin-lancing medium against a skin surface to form an incision therein and then remove the skin-lancing medium from the incision. A stimulator member is mounted to the housing at the open end thereof for movement relative to the housing. The stimulator member extends about a longitudinal axis of the housing and is adapted to engage the skin surface to bulge and open the incision in response to a pressing of the end face against the skin surface.

The invention also relates to a device for expressing body fluid from a lanced skin surface, which comprises a housing, and a stimulator mechanism mounted to the housing at an end thereof. The stimulator mechanism includes a generally circular array of stimulator elements each mounted to the housing for movement toward and away from a longitudinal axis of the housing. An actuator is mounted to the housing for displacing the stimulator elements toward the axis.

The invention also relates to a device for expressing body fluid from a lanced skin surface, which comprises a housing and a stimulator member mounted on the housing at an end thereof. The stimulator member comprises a coil spring which is compressible toward the housing in response to being pushed against a user's skin in surrounding relationship to a lanced portion thereof.

Another aspect of the invention relates to a device for expressing body fluid from a lanced skin surface which comprises a housing and a hollow stimulator member mounted at an end of the housing and adapted to engage a user's skin surface in surrounding relationship to a lanced portion thereof. In order to promote the flow of body fluid, the stimulator member can be heated, or vibrated. If vibrated, the stimulator member applies an ultrasonic frequency to the skin surface.

The invention also relates to a device for expressing body fluid from a lanced skin surface which comprises a housing and a hollow stimulator member mounted at an end of the housing for longitudinal movement relative to the housing and adapted to contact a user's skin surface in surrounding relationship to a lanced portion thereof. A motor is mounted in the housing and a reciprocatory mechanism is connected to the motor to be driven thereby, and is operably connected to the stimulator member for reciprocating the stimulator member along a longitudinal axis of the stimulator member.

BRIEF DESCRIPTION OF THE DRAWING

The objects and advantages of the invention will become apparent from the following detailed description of preferred embodiments thereof in connection with the accompanying drawing in which like numerals designate like elements and in which:

FIG. 7 is a fragmentary longitudinal sectional view through a second embodiment of the invention;

FIG. 8 is a fragmentary longitudinal sectional view taken through a third embodiment of the invention;

FIG. 9 is a side elevational view of a fourth embodiment of the invention pressed against a skin surface;

FIG. 10 is an end view of the device depicted in FIG. 9;

FIG. 11 is a view similar to FIG. 9 after the device has been compressed against the skin surface to bulge and open an incision;

FIG. 12 is an end view of the device in the condition depicted in FIG. 11;

FIG. 18 is a side elevational view, partly in longitudinal section of yet another embodiment of the invention; and FIG. 19 is a longitudinal sectional view taken through still a further embodiment of the invention.

DETAILED DESCRIPTION OF A PREFERRED EMBODIMENT OF THE INVENTION

Figure 1:
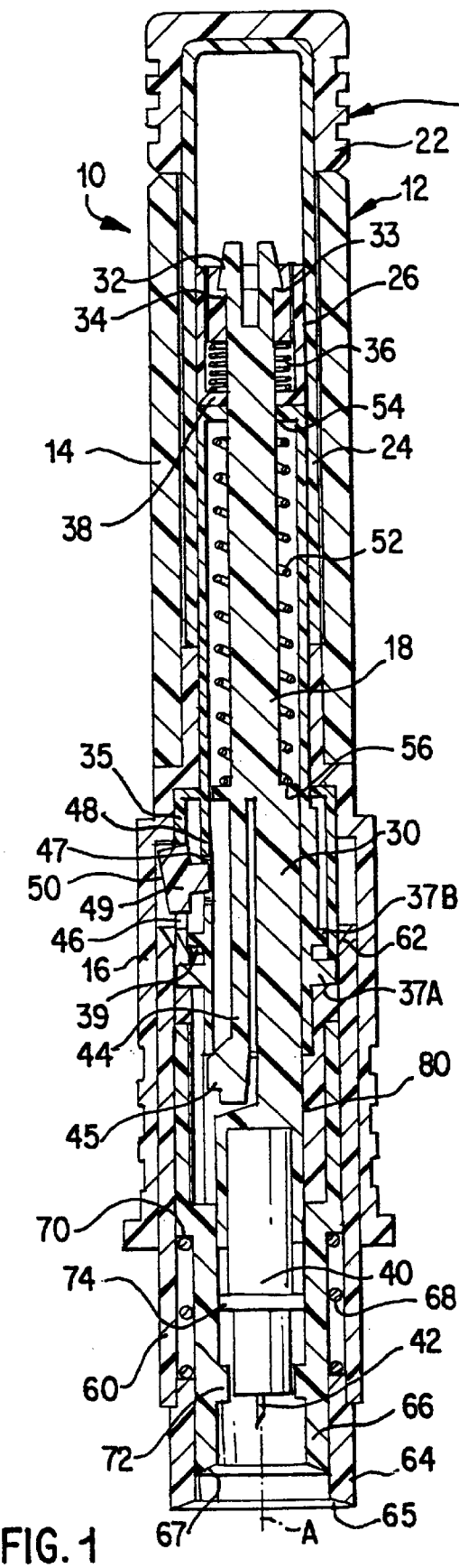
FIG. 1 is a longitudinal sectional view through a blood sampling device according to a first embodiment of the invention, with the lancet carrier in an unarmed condition.

A lancing device 10 (see FIG. 1) according to one preferred embodiment of the invention comprises an outer housing 12 having upper and lower portions 14, 16 connected together, and an inner housing 18 fixed to the outer housing.

Mounted for vertical reciprocation in the upper portion 14 of the outer housing 12 is a cocking mechanism 20 comprising a pull handle 22 to which is fixedly secured a hollow draw tube 24. Fixed to an inner wall of the draw tube 24 is a draw ring 26.

Situated within the draw tube 24 is a draw bar 30 having a pair of flexible hooks 32 at its upper end. The hooks are releasably latched to a sleeve 34 which is movably disposed within the draw ring 26. A coil compression spring 36 acts between a flange 33 of the sleeve 34 and an inner flange 38 of the draw ring 26.

A trigger sleeve 35 is mounted within the lower portion 16 of the outer housing 12. A lower end of the trigger sleeve rests upon a first outer flange 37A of the inner housing, and a second outer flange 37B of the inner housing rests upon an inner projection 39 of the trigger sleeve.

At its lower end the draw bar 30 frictionally holds a skin-lancing medium in the form of a disposable lancet 40 in which a needle 42 is disposed. The draw bar 30 includes a flexible latch finger 44 that has a projection 45 adapted to be received in a hole 46 of the inner housing 18 (see FIG. 2) when the device is armed. A trigger member 49 is mounted in a hole 47 of the trigger sleeve 35 and includes an arm 48 extending partially into the hole 46. The trigger 46 includes an inclined cam follower surface 50.

A coil compression spring 52 acts between a top wall 54 of the inner housing 18 and a shoulder 56 of the draw bar.

Slidably disposed within a lower end of the lower portion of the outer housing is a firing tube 60 which includes an upper cam surface 62. Fixed to a lower end of the firing tube 60 is an outer hollow stimulator member in the form of a cylindrical ring 64, having an end surface 65 of generally frusto-conical shape so as to be oriented at a downward and inward inclination to generally face a longitudinal axis A of the device.

Disposed coaxially within the firing tube 60 and outer stimulator ring 64 is an inner hollow stimulator member also in the form of a cylindrical ring 66 having a frusto-conical end surface 67 also oriented at a downward and inward inclination.

The end surfaces 65 and 67 are of circular configuration when viewed along the axis A, other configurations, such as polygonal, oval, etc., are possible.

A coil compression spring 68 acts between an upper end of the outer stimulator ring 64 and a downwardly facing shoulder 70 of the inner stimulator ring 66.

The inner stimulator ring 66 includes a lance stop flange 72 adapted to be engaged by a lance ring 74 of the lancet 40 as will be explained.

The first flange 37A of the inner housing rests upon a support sleeve 80 which, in turn, rests upon an upper end of the inner stimulator ring 66.

Figure 2:
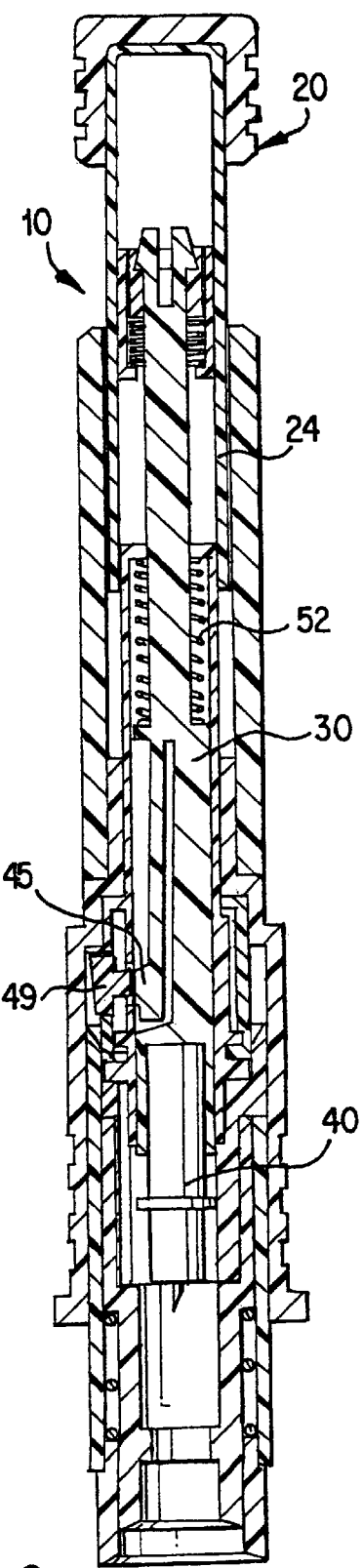
FIG. 2 is a view similar to FIG. 1, with the lancet carrier in an armed condition.

In practice, when a fluid sample, such as blood or interstitial fluid, is to be taken from a user's body, a lancing device according to the present invention can be used to minimize pain. To do so, a region of the user's body having less sensitivity than, for example, a fingertip, is selected. Such a low-sensitivity region could be the user's forearm for example. Initially, the handle 22 is pulled up to raise the drawbar 30 until the projection 45 of the latch finger 44 snaps into the hole 44 of the inner housing 18, as shown in FIG. 2. Simultaneously, the spring 52 is compressed.

Figure 3:
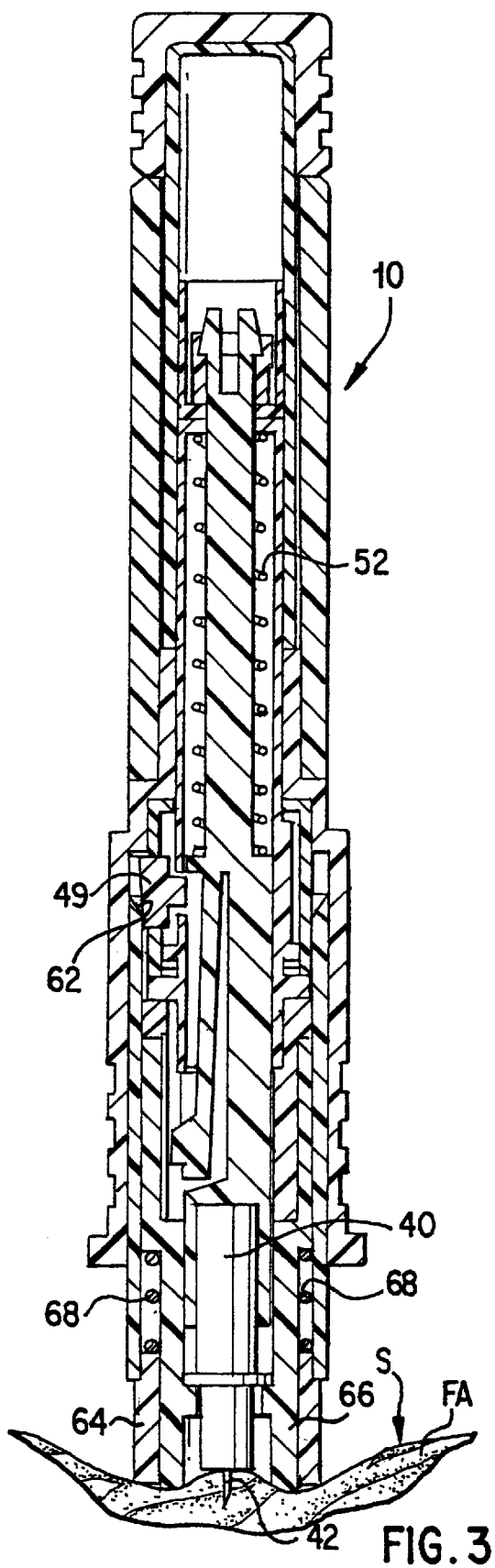
FIG. 3 is a view similar to FIG. 2 after the lancet carrier has been triggered and a lancet is penetrating the skin.

If the outer stimulator ring 64 is pressed against the user's skin S, e.g., on the selected forearm region FA, the ring 64 and its cam surface 62 are moved upwardly to displace the trigger radially inwardly, whereupon the projection 45 of the latch finger 44 is disengaged from the hole 46. Accordingly, the spring 52 expands to displace the drawbar 30 downwardly so that the needle 42 punctures the skin sufficiently deep to cut capillaries in the superficial vascular plexus, as shown in FIG. 3. Simultaneously, the spring 68 is compressed. The extent of displacement of the drawbar 30 is limited by engagement between the lance ring 74 with the lance stop 72.

Figure 4:
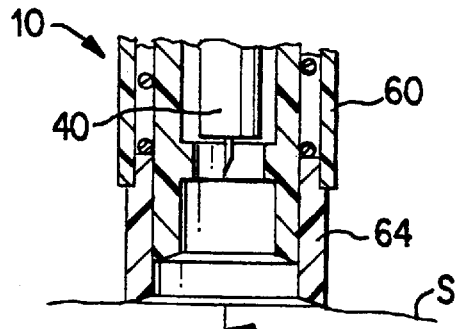
FIG. 4 is a fragmentary view similar to FIG. 1 after an incision has been formed.

Once lancing has occurred, the compressed spring 68 expands to raise the drawbar, as well as the needle 42 and inner stimulator ring 66 from the skin (see FIG. 4).

Figure 5:
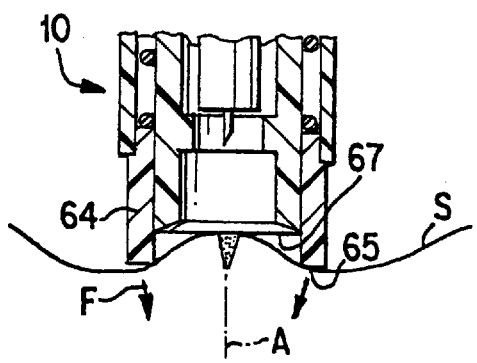
FIG. 5 is a view similar to FIG. 4 showing a stimulator member of the device being depressed to cause the incision to bulge and open.

The user then alternately applies and releases a downward force on the outer housing 12. Each time that a downward force is applied, the end face 65 of the outer stimulator ring 64 exerts a downward force F which depresses a ring-shaped portion of the skin and body tissue which is disposed in surrounding relationship to the wound or incision I, causing the wounded area to bulge while pulling apart the sides of the wound (see FIG. 5). Hence, fluid such as blood or interstitial fluid is trapped and pressurized so that it travels upwardly through the pulled-open end of the wound since the surrounding ring of depressed skin and body tissue restricts the outward flow of fluid. That action is enhanced by the fact that the force F is inclined inwardly toward the axis A to force the fluid toward the bulged area.

Figure 6:
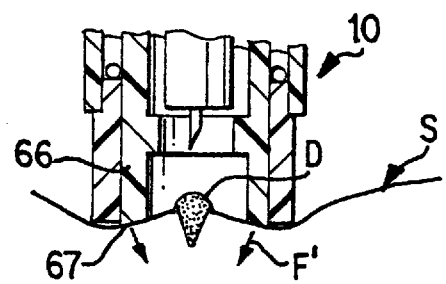
FIG. 6 is a view similar to FIG. 5 after a stimulating action has been performed to form a drop of blood at the open end of the incision.

When the downward force is released, the sides of the wound close, and fresh fluid flows toward the area of the wound to replace fluid which had been forced upwardly through the wound. As the downward force is reapplied, the above-described action is repeated and additional fluid is forced through the wound. Eventually, this "pumping" action results in the formation of a suitably large drop D of fluid (FIG. 6).

It will thus be appreciated that the present invention enables an ample supply of blood, interstitial fluid or other body fluid to be obtained relatively painlessly from areas of the body which typically possess lesser amounts of such fluid as compared with the highly sensitive fingertip region.

Note that each time that the downward force is applied to the outer housing, the outer stimulator ring 64 moves upwardly relative to the inner stimulator ring 66 so that the end surface 67 of the inner ring 66 also contacts the skin surface S at a location inwardly of the outer face 65, thereby promoting the displacement of fluid inwardly toward the wound. However, the present invention can be practiced by a single stimulator ring arrangement 64A as shown in FIG. 8.

While the surfaces 65, 67 are continuous, i.e., non-interrupted, it may be desirable to provide either or both of those surfaces with circumferentially spaced recesses 80 as shown in FIG. 7. The surface(s) 65A, 67A will still depress a ring of body tissue surrounding the wound, but the areas of the ring corresponding to the location of the recesses will be depressed to a lesser extent than the other areas. Those lesser depressed areas will provide less resistance to fluid flow and will thus enable some fluid to leak past the ring, which would be beneficial in the event that the user neglects to release the downward pressure on the device.

The stimulator member need not be in the form of a ring. As depicted in FIGS. 9–12, the stimulator member can be in the form of a helical spring 90 formed by a flat strip 92. Such a spring would function in somewhat similar fashion to the double-ring arrangement of FIGS. 1–7 in that a stimulator surface gradually comes into contact with the skin in a radially inward direction to aid in propelling blood or interstitial fluid toward the center axis. In that regard, FIGS. 9 and 10 depict a condition when the spring 90 is uncompressed. In contrast, FIGS. 11 and 12 depict a condition wherein the spring is fully compressed. Shaded regions in FIGS. 10 and 12 represent contact between the spring and the skin. It will be appreciated that during compression of the spring, the contact region of the spring progresses gradually radially inwardly, causing blood or interstitial fluid to be pushed toward the axis A and thus toward the bulged area of the skin.

Figure 13:
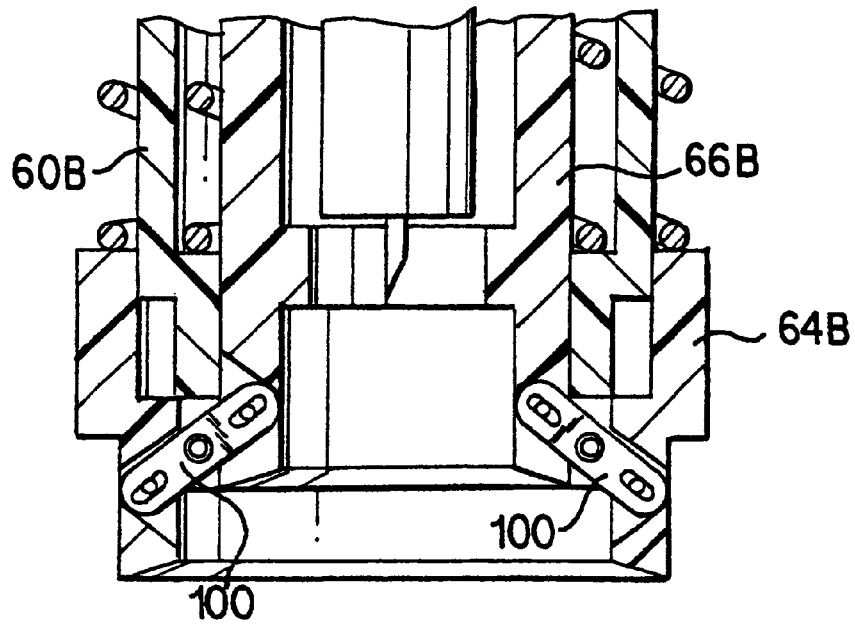
FIG. 13 is a fragmentary longitudinal sectional view taken through a fifth embodiment of the invention while in a first state of operation.
Figure 14:
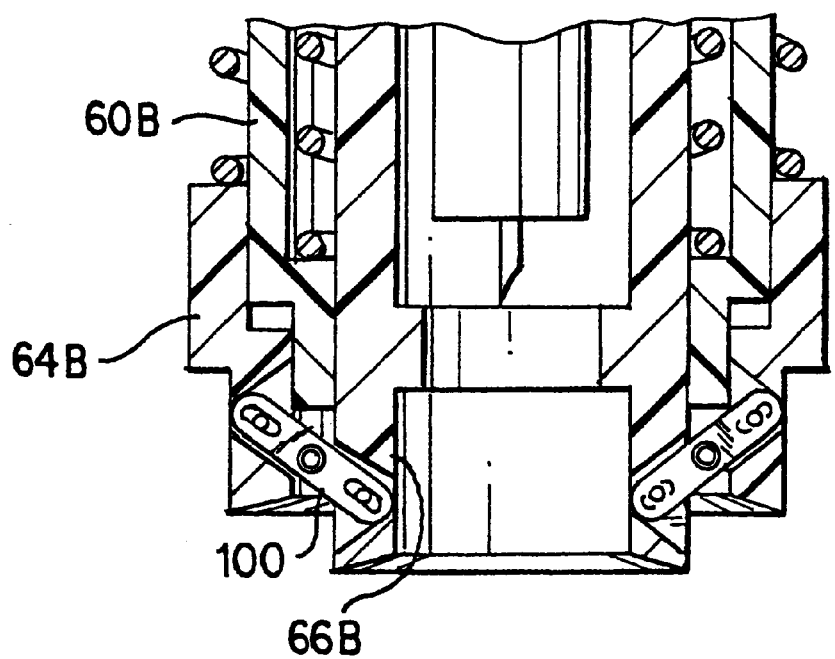
FIG. 14 is a view similar to FIG. 13 with the device in a second condition of operation.

Depicted in FIGS. 13 and 14 is yet another alternative embodiment wherein the outer stimulator ring 64B is interconnected to the inner stimulator ring 66B by levers 100 which are pivoted to the firing tube 60B. Thus, upward sliding movement of the outer ring 64B is transmitted as a downward force to the inner ring 66B to slide the latter downwardly and intensify the pumping action.

Figure 15:
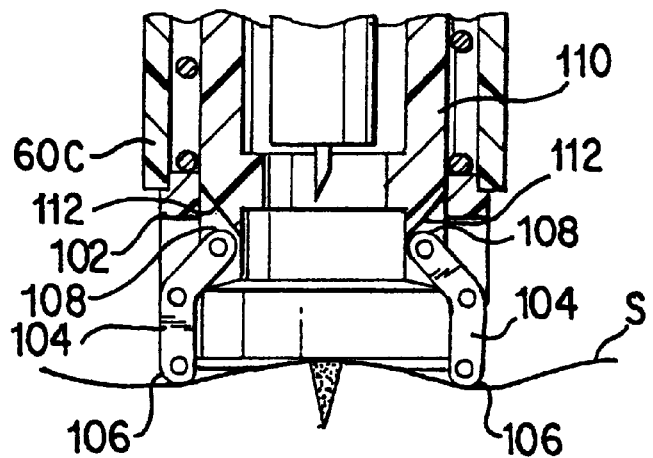
FIG. 15 is a fragmentary longitudinal sectional view taken through a sixth embodiment of the invention in a first condition of operation thereof.
Figure 16:
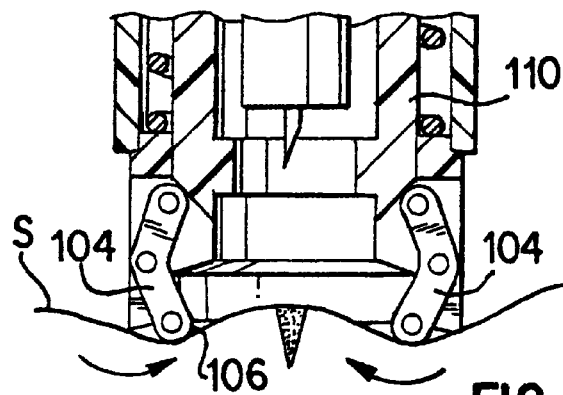
FIG. 16 is a view similar to FIG. 15 with the device in another condition of operation.
Figure 17:
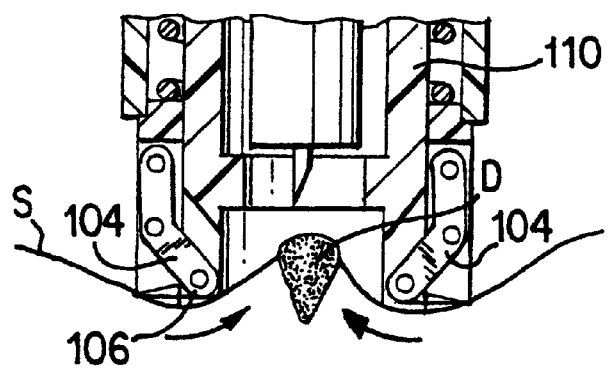
FIG. 17 is a view similar to FIG. 16 of yet a further condition of operation of the device.

A further embodiment is depicted in FIGS. 15–17 wherein the firing tube 60C has a carrier tube 102 affixed at a lower end thereof. Pivotably mounted on the carrier tube 102 is a circular array of levers 104 each having an upper and lower end, each lower end carrying a stimulator element in the form of a roller 106. Each lever 104 is rotatable about an axis extending orthogonally relative to the axis of the housing.

An inner ring 110 is slidable up and down, either by manual force, or by a motor-driven cam (e.g., of the type disclosed later in connection with FIG. 19). That ring 110 has a beveled cam face 112 formed on its lower end. When the device is pressed against the skin, following a lancing procedure, the ring 110 is moved downwardly so that the cam face 112 engages rollers 108 mounted on upper ends of the levers. Hence, the levers 104 are rotated such that the lower rollers 106 are displaced inwardly and upwardly at a location disposed below the open end of the bulged wound to open the wound and force blood or interstitial fluid toward the wound to form a drop D. When the levers are not contacted by the cam face 112, the rollers 106 gravitate to a rest position shown in FIG. 15. Repeated applications of the downward force cause the drop to become gradually enlarged as explained earlier.

Depicted in FIG. 18 is an alternative embodiment similar to that depicted in FIGS. 1–6, except that the lower end surface of the outer stimulator ring 64D is provided with a hollow stimulator element 114 which is electrically connected to a battery 116 mounted in an upper end of the device. The element can be either an electrical resistance element (i.e., a heater) or a vibrator such as a piezoelectric transducer, intended to stimulate fluid flow. A heater will expand the capillaries and make the blood or interstitial fluid less viscous and thus more flowable, in order to increase the amount of the body fluid sample.

On the other hand, if the element 114 is a vibrator, such as a piezoelectric transducer, vibrations can be created which stimulate the flow of body fluid. This could be achieved by operating the transducer to produce frequencies below 28,000 cycles per second. Alternatively, ultrasonic frequencies, i.e., frequencies above 20,000 cycles per second, will create interferometric wave patterns inside the skin that cause contractions forcing fluid upwardly from the wound. The frusto-conical shape 114A of the end face of the element will optimize the creation of such wave patterns. It may be further beneficial to employ a heater, such as an infrared emitter, mounted in the housing which vasodilates the capillaries to increase blood flow. Another advantage of the use of such frequencies is that only minimal downward force to the device may be necessary since the wave patterns may produce an ample pumping action.

FIG. 19 depicts a device which is not automatically fired, but rather requires manual actuation of lever 130 against a bias of a spring 132 to force a trigger 134 to push a projection 136 out of a hole 138 (when the projection extends into that hole).

Mounted in a housing 140 of the device are a battery 142 and electric motor 144 connected to the battery to be actuated thereby. The motor 144 rotates a sleeve 146 about the axis A. The sleeve includes a cam surface 148 which engages a follower roller 150 mounted on a tube 152.

As the sleeve 146 rotates, the cam surface pushes the tube 152 downwardly against the bias of a coil compression spring 154, to push an inner stimulator ring 156 repeatedly against a skin surface, thereby pumping blood to the top of an incision in the same manner described earlier herein. The inner stimulator ring 156 reciprocates along the axis A within an outer stimulator ring 155. This embodiment eliminates the need for the user to pulsate the device up and down; the pumping operation is achieved automatically in response to actuation of the lever 130.

The cam mechanism 146 can be used in an automatically firing device, such as that disclosed in connection with FIG. 1.

It will be appreciated that the present invention enables a sampling of blood or interstitial fluid to be taken from areas of the body, such as a forearm, that are less insensitive to pain, despite the fact that those areas typically have relatively less fluid as compared, for example, to fingertips (which are highly sensitive to pain).

Therefore, there will be less reluctance on the part of users to have a sampling procedure performed. For example, diabetics who experience a relatively high fear of pain will be less likely to neglect monitoring their blood glucose levels.

Another suitable skin lancing device that can be used to practice the present invention is that disclosed in concurrently filed application Ser. No. 08/857,680, the disclosure of which is incorporated herein by reference.

In lieu of using a lancet as a skin-lancing medium, other skin-lancing media can be used, such as a laser, or known pneumatic or hydraulic injectors of the type which inject pressurized gas or liquid against the skin. Such auto injectors are sold by Becton-Dickinson, for example, to inject insulin. By eliminating the insulin and merely injecting the gas (e.g., air or nitrogen) or liquid (e.g., water) at pressures above 30 psi. an incision could be formed in the skin for taking samples of body fluid. Advantageously, small particles could be mixed with the gas to promote the tissue-cutting action. The particles could comprise carbon particles of from 1 micron to 0.010 inches in diameter.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed:

1. A device for expressing whole capillary blood from a lanced skin surface comprising:
    A) a housing;
    B) a stimulating member mounted at least partially within the housing, the stimulator member comprising a stimulating end adapted to surround an incision to manipulate the skin surface by opening the incision so as to fill the incision with blood when the stimulating end is pressed against the skin surface, the stimulating member being longitudinally slidable relative to the housing such that by repeatedly pressing the stimulator member against the surface of the skin, a sample of blood is expressed from the incision.

2. The device in accordance to claim 1, wherein the stimulating member comprises concentric inner and outer separate stimulating sleeves, where the outer sleeve engages the skin surface first and the inner sleeve second to manipulate the skin and force blood into the incision as the incision is opened and force the blood to the surface of the skin as the incision closes.

3. The device in accordance to claim 1, wherein the stimulating member comprises concentric inner and outer separate stimulating sleeves, where the inner sleeve engages the skin surface first and the outer sleeve second to manipulate the skin and force blood into the incision as the incision is opened and force the blood to the surface of the skin as the incision closes.

4. A method of obtaining a sample of capillary whole blood from the body, comprising the steps of:
    A) applying a skin-lancing medium against the skin of a user to form an incision in the skin;
    B) applying a force by depressing the skin in a manner to form a depressed ring of body tissue in surrounding relationship to the incision to manipulate the incision open;
    C) releasing the force of step B; and
    D) repeating steps B) and C) a sufficient number of times to express a sample of blood from the incision.

5. A device for expressing body fluid from a lanced skin surface, comprising:
    a housing; and
    a stimulator mechanism mounted to the housing at an end thereof, the stimulator mechanism extending from the end of the housing for contacting the skin including a generally circular array of stimulator elements each mounted to the housing for movement toward and away from a longitudinal axis of the housing.

6. The device according to claim 5, wherein the stimulator elements comprise rollers mounted to the housing by pivoted levers.

7. The device according to claim 5, further including a lancet carrier mounted in the housing and adapted to support a disposable lancet; and a drive mechanism in the housing for driving the lancet carrier along a longitudinal axis of the housing to lance a skin surface and form an incision therein.

8. A device for expressing body fluid from a lanced skin surface comprising:
    a housing;
    a stimulator member mounted on the housing at an end thereof, the stimulator member comprising a coil spring compressible toward the housing in response to being pushed against the skin in surrounding relationship to a lanced portion thereof.

9. A device for expressing body fluid from a lanced skin surface comprising:
    a housing;
    a hollow stimulator member mounted at an end of the housing and adapted to engage the skin surface in surrounding relationship to a lanced portion thereof;
    and heating means for heating the stimulator member.

10. The device according to claim 9, wherein the heating means comprises a battery mounted in the housing and electrically connected to the stimulator member.

11. A device for expressing blood or interstitial fluid from a lanced skin surface, comprising:

a housing;

a retractable skin lancing mechanism mounted in the housing;

a hollow stimulator member mounted on the housing at an end thereof and adapted to engage the skin surface in surrounding relationship to a lanced portion thereof, the stimulator member operable to apply an ultrasonic frequency to the skin surface.

12. The device according to claim 11, wherein the stimulator member comprises a piezoelectric transducer.

13. The device according to claim 12, wherein the transducer is ring-shaped and includes a frusto-conical inner surface.

14. A device for expressing body fluid from a lanced skin surface comprising:

a housing;

a skin lancing mechanism mounted in the housing;

a hollow stimulator member mounted at an end of housing for longitudinal movement relative to the housing and adapted to contact the skin surface in surrounding relationship to a lanced portion thereof;

a motor mounted in the housing; and a reciprocatory mechanism connected to the motor to be driven thereby and operably connected to the stimulator member for reciprocating the stimulator member along a longitudinal axis of the stimulator member.

* * * * *